(12) United States Patent
Desilets et al.

(10) Patent No.: US 8,070,691 B2
(45) Date of Patent: Dec. 6, 2011

(54) CYTOLOGY DEVICE

(75) Inventors: David J. Desilets, Springfield, MA (US); Richard W. Ducharme, Winston-Salem, NC (US)

(73) Assignees: Cook Medical Technologies LLC, Bloomington, IN (US); Baystate Health, Inc., Springfield, MA (US)

( * ) Notice: Subject to any disclaimer, the term of this patent is extended or adjusted under 35 U.S.C. 154(b) by 0 days.

(21) Appl. No.: 12/331,123

(22) Filed: Dec. 9, 2008

(65) Prior Publication Data

US 2010/0145225 A1    Jun. 10, 2010

(51) Int. Cl.
*A61B 10/00* (2006.01)
(52) U.S. Cl. ........................................ 600/570
(58) Field of Classification Search .......... 600/562–570, 600/434; 606/160; 132/74.5, 76.4; 401/185, 401/206, 207; 15/118; D24/147
See application file for complete search history.

(56) References Cited

U.S. PATENT DOCUMENTS

| 2,746,461 | A | * | 5/1956 | Bocchino | 132/74.5 |
| 2,955,592 | A | * | 10/1960 | MacLean | 600/569 |
| 4,936,312 | A | * | 6/1990 | Tsukagoshi | 600/562 |
| 5,201,323 | A | * | 4/1993 | Vermeulen | 600/569 |
| 5,807,282 | A | | 9/1998 | Fowler | |
| 5,951,490 | A | | 9/1999 | Fowler | |
| 2007/0167868 | A1 | | 7/2007 | Sauer | |
| 2008/0183100 | A1 | | 7/2008 | Hardin | |

FOREIGN PATENT DOCUMENTS

| WO | WO 97/24071 | 7/1997 |
| WO | WO 00/24321 | 5/2000 |
| WO | WO 2008/073792 A1 | 6/2008 |

* cited by examiner

*Primary Examiner* — Brian Szmal
(74) *Attorney, Agent, or Firm* — Brinks Hofer Gilson & Lione

(57) ABSTRACT

A cytology device and a method of use thereof are described. The cytology scraper comprises a scraping element that provides increased tissue removal capabilities over conventional cytology brushes. The edges of the scraping element can also simultaneously dilate strictures during the tissue removal procedure.

20 Claims, 7 Drawing Sheets

CYTOLOGY DEVICE

TECHNICAL FIELD

The invention generally relates to a cytology device.

BACKGROUND

Conventional cytology devices in the biliary and pancreatic ducts include cytology brushes and forceps. Such brushes and forceps have proven to provide poor tissue cell yields for tissue sampling. Additionally, conventional cytology devices are not capable of navigating remote body cavities, such as the gastrointestinal cavity. Additionally, the anatomy of the gastrointestinal cavity contains many tortuous body lumens which can make accessing these cavities difficult.

SUMMARY

Accordingly, a cytology scraper is provided that addresses one or more of the needs described above.

In a first aspect of the invention, a cytology device is provided. The cytology device comprises a helically coiled cable. The cable comprises torsional rigidity sufficient to transfer rotational motion from a proximal portion of the cable to a distal portion of the cable, the distal portion adapted to be introduced into a body lumen, and the proximal portion adapted to remain outside of the lumen so as to allow manipulation of the distal portion. A scraper element is operably connected to the distal portion. The scraper element comprises at least one cutting edge configured to excise tissue cells upon rotational movement of the scraper element. A reservoir is also provided that is adapted to receive the excised tissue.

In a second aspect of the invention, a cytology device is provided comprising a helically coiled cable. The coiled cable comprises torsional rigidity sufficient to transfer rotational motion from a proximal portion of the cable to a distal portion of the cable. A scraper element is operably connected to the distal portion, the scraper element comprising at least one cutting edge configured to excise tissue cells upon rotational movement of the scraper element. A reservoir is adapted to receive the excise tissue. A retractable outer sheath is disposed over the scraping element for retaining excised tissue within the reservoir.

In a third aspect of the invention, a method of performing a cytology procedure is described. A cytology device is provided. The device comprises a helically coiled cable comprising torsional rigidity sufficient to transfer rotational motion from a proximal portion of the cable to a distal portion of the cable, the distal portion adapted to be introduced into a body lumen, the proximal portion adapted to remain outside of the lumen so as to allow manipulation of the distal portion. A scraper element is operably connected to the distal portion, the scraper element comprising at least one cutting edge configured to excise tissue cells upon rotational movement of the scraper element. A reservoir is adjacent to the at least one cutting edge and adapted to receive the excise tissue. The cytology device is advanced to the target tissue site. The proximal portion of the coiled cable is rotated so as to engage and excise the target tissue with the cutting surfaces. The tissue is collected in the reservoir.

BRIEF DESCRIPTION OF THE DRAWINGS

Embodiments will now be described by way of example with reference to the accompanying drawings, in which.

DETAILED DESCRIPTION

The embodiments are described with reference to the drawings in which like elements are referred to by like numerals. The relationship and functioning of the various elements of the embodiments are better understood by the following detailed description. However, the embodiments as described below are by way of example only, and the invention is not limited to the embodiments illustrated in the drawings. It should also be understood that the drawings are not to scale and in certain instances details have been omitted, which are not necessary for an understanding of the embodiments, such as conventional details of fabrication and assembly.

Figure 1:
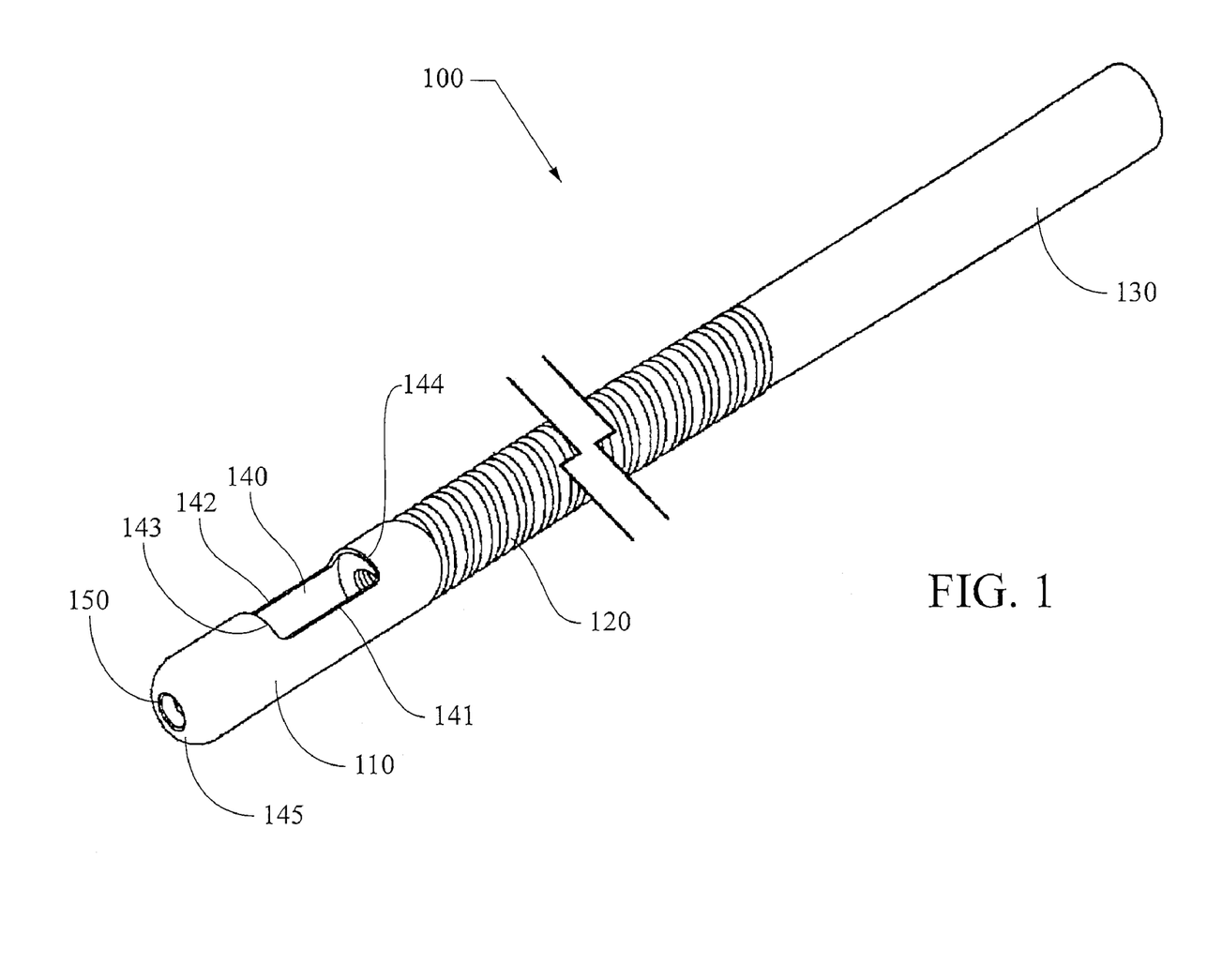
FIG. 1 is a pictorial view of a cytology scraper comprising a scraper element, a coiled shaft, and a handle.

An exemplary cytology scraper is shown in FIG. 1. FIG. 1 shows a pictorial view of a cytology scraper 100 that includes a scraping element 110, a coiled shaft, 120, and a handle 130. In general, the cytology scraper 100 can be navigated and maneuvered to gain access to remote body cavities, such as, for example, a biliary or pancreatic duct. After reaching a target tissue site, the scraping element 110 engages the target tissue and removes a desired amount of the tissue for sampling. Various techniques may be used to remove the tissue cells. In one example, the handle 130 may be grasped to rotate the scraping element 110 against the target tissue, thereby removing tissue cells. After the cells have been removed, they enter a reservoir 140. Additionally, the scraping element 110 may also assist in dilating strictures that may impede passage through the body lumen.

Scraping element 110 may be generally cylindrical-shaped, as shown in FIG. 1. Other shapes of the scraping element 110 are contemplated. A proximal end of the scraping element 110 is affixed to a distal end of the coiled shaft 120. Scraping element 110 is shown to have an atramautic distal tip 145 in which the distal end of the scraping element 110 tapers inward. The scraping element 110 comprises a reservoir 140 for receiving removed tissue cells. The reservoir 140 is shown to be bounded by edges 141, 142, 143, and 144. Any portion of the scraping element 110 may be used to engage target tissue or strictures. Preferably, one or more of the edges 141, 142, 143, and 144 contacts a target tissue site and scrapes away tissue cells. For example, one or more of the edges 141, 142, 143, and 144 may engage the target tissue as the scraping element 110 is rotated clockwise and/or counterclockwise. Alternatively, the one or more edges 141, 142, 143, and 144 may engage the target tissue via back and forth movements of the scraping element 110 to scrape and peel away cells. Any combination of back and forth movements and rotation may be used to scrape and peel away tissue cells.

An aperture 150 is shown at the distal end of the scraping element 110. The aperture 150 extends into a lumen which extends along a longitudinal axis of the cytology scraper 100. The aperture 150 provides an opening through which a wire guide may extend.

Figure 2:
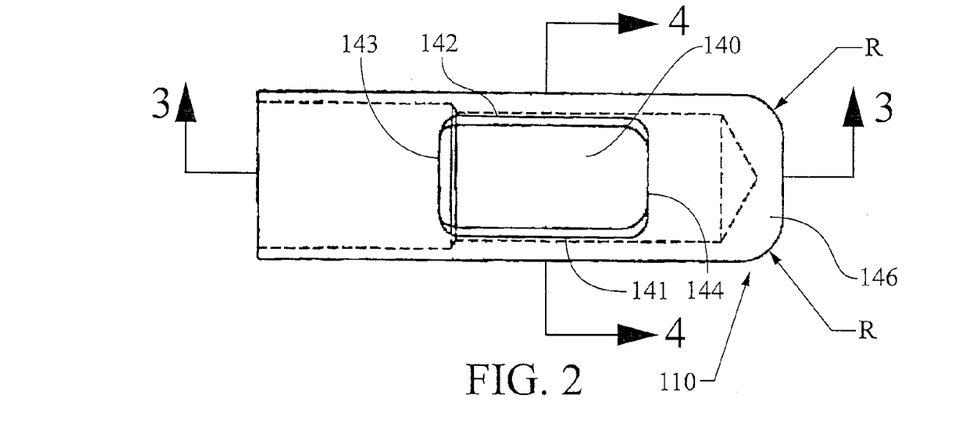
FIG. 2 is a top view of the scraping element of FIG. 1 having a distal opening for a wire guide to extend therethrough.
Figure 3:
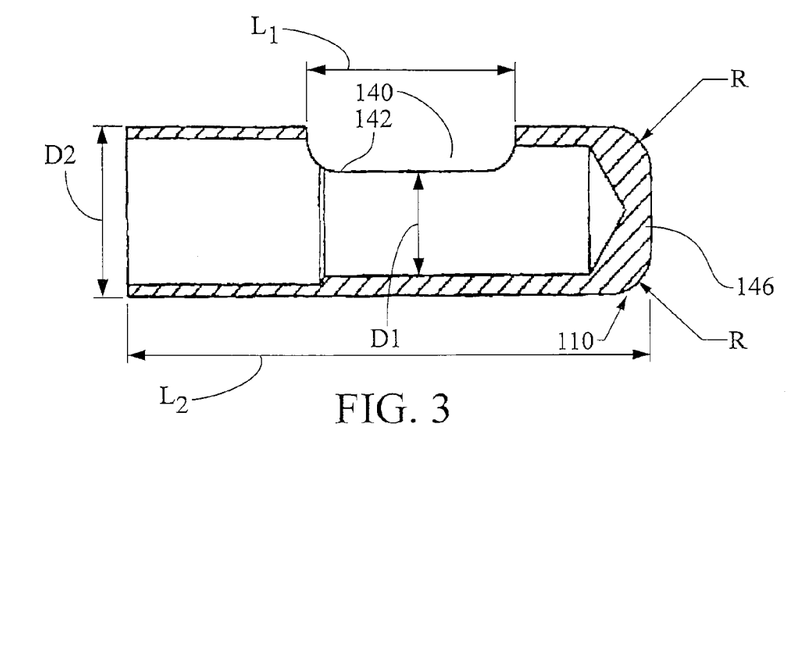
FIG. 3 is a sectional view of Figure taken along line 3-3.
Figure 4:
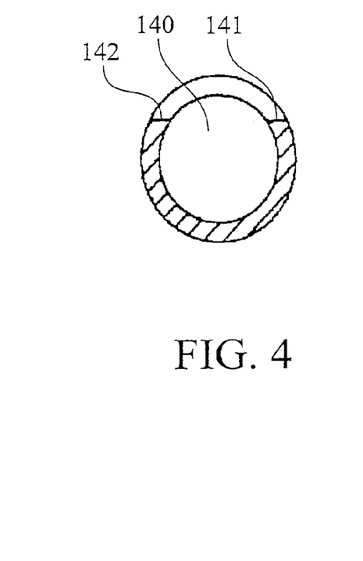
FIG. 4 is an end sectional view of FIG. 3.

FIGS. 2-4 show a blown-up view of the scraping element 110 of FIG. 1. The reservoir 140 comprises vertical edges 143 and 144 which extend deeper into the body of the scraping element 110 relative to that shown in FIGS. 5-7. The greater length of the vertical edges 143 and 144 relative to that of FIGS. 5-7 may translate into greater scraping or excising ability. The reservoir 140 also comprises horizontal edges 141 and 142 which are parallel to the longitudinal axis of the scraping element 110. FIG. 4 illustrates that the reservoir 140 is symmetrical about the longitudinal axis of the scraping element 110. FIG. 4 shows that the edges 141 and 142 are symmetrical relative to each other and in the same plane.

Additionally, FIGS. 2-3 indicate that the scraping element 110 comprises an aperture 150 at its distal end through which a wire guide may extend. The aperture 150 may be sized to receive the wire guide. The embodiment of FIGS. 2-4 show that the aperture 150 may be sized to receive a standard wire guide having a diameter of about 0.035 inches. Alternatively, the aperture 150 may be varied in size to receive wire guides greater than or less than 0.035 inches. Suitable dimensions of the scraping element 110 and the reservoir 140 will vary depending on numerous factors, including the size and location of the target tissue to be removed as well as the difficulty in scraping away the target tissue cells from the target tissue site.

Figure 5:
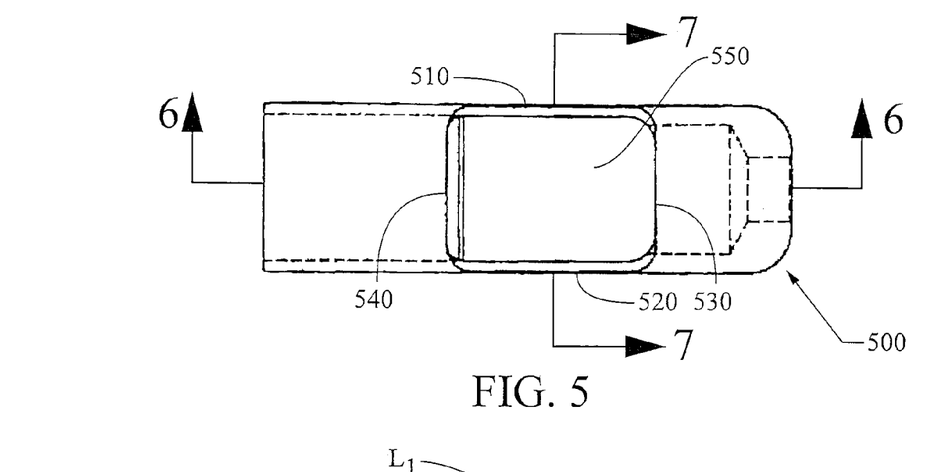
FIG. 5 is an alternative embodiment of a scraping element having a solid tip and a reservoir.
Figure 6:
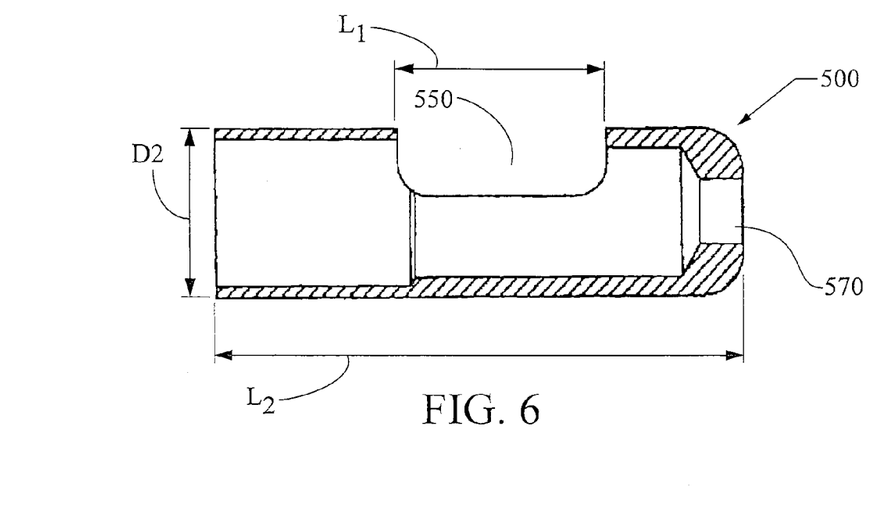
FIG. 6 is a sectional view of FIG. 5 taken along line 6-6.
Figure 7:
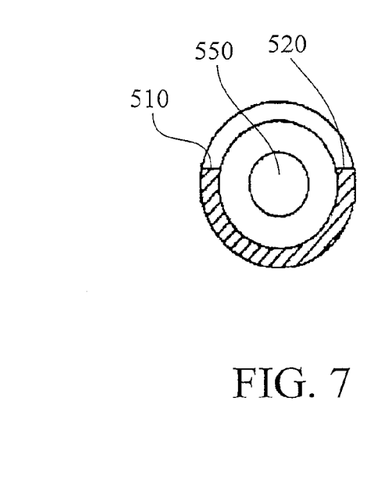
FIG. 7 is an end sectional view of FIG. 6.

In an alternative embodiment, the scraping element may comprise a solid distal tip, as shown in FIGS. 5-7. FIG. 5 is a top view of a scraping element 510. The scraping element 510 comprises a solid distal tip 546 and a reservoir 540. The reservoir 540 is characterized by a partial opening along the scraping element 510 and extends deeper than the reservoir 140 of FIGS. 1-4. The reservoir 540 is shown bounded by vertical edges 543 and 544, longitudinal edges 541 and 542, and a bottom surface 568 shown in FIG. 6. FIG. 5 shows that the edges 541 and 542 are chamfered and are substantially parallel to a longitudinal axis of the cytology scraper 510. FIG. 7 shows that the edges 541 and 542 reside in the same plane. Edges 543 and 544 are shown extend vertically and substantially perpendicular to the longitudinal axis of the cytology scraper 510. FIG. 7 illustrates that the edges 541 and 542 of the reservoir 540 are symmetrical relative to each other. The reservoir 540 enables retention of tissue cells therewithin after the one or more edges 541-544 have scraped away tissue cells from a target site.

Suitable dimensions of the scraping element 510 and the reservoir 540 will vary depending on numerous factors, including the size and location of the target tissue to be removed. In the example shown in FIGS. 5-7, the reservoir 540 downwardly extends to a predetermined depth of $D_1$ (FIG. 3) that may range from about 0.035 inches to about 0.095 inches. The reservoir 540 may also be characterized by a longitudinal length $L_1$, which may range from about 0.140 inches to about 0.160 inches.

The scraping element 510 may include a radius of curvature, R, a longitudinal length, $L_2$, and an outer diameter $D_2$. The radius of curvature, R, is shown at the distal end 546 of the scraping element 510 to create a rounded end. Such a rounded end reduces friction thereby creating an atraumatic distal end as the scraping element 510 advances through an endoscope and into a body lumen. In the examples of FIGS. 5-7, the radius of curvature may vary from about 0.025 inches to about 0.035 inches. The longitudinal length $L_2$ may vary from about 0.244 inches about 0.444 inches. The outer diameter $D_2$ of the scraping element 510 may vary from about 0.100 inches to about 0.120 inches. In one example, the outer diameter is about 0.110 inches. The outer diameter may range from about 4 FR to about 11.5 FR, and more preferably between about 8.5 FR to about 11.5 FR. Retention of the tissue cells within the reservoir 540 may be enhanced by the distal most section of the scraping element 510 being solid, as shown in FIG. 6. The solid section of the scraping element 510 may enhance the entrapment of tissue cells within the reservoir 540. The deeper reservoir 540 compared to that of FIGS. 1-4 may enable greater accumulation and retention of tissue cells. Additionally, the solid section of the scraping element 510 at distal end 546 provides additional surface area for scraping and removing tissue cells into the reservoir 540.

Figure 8:
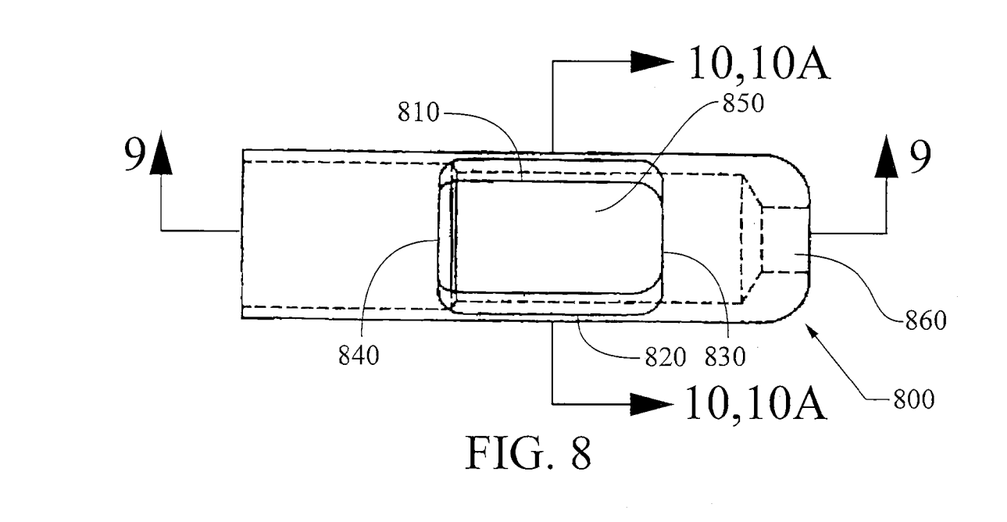
FIG. 8 is a top view of a cytology scraper in which the scraping edges are at different height.
Figures 9, 10:
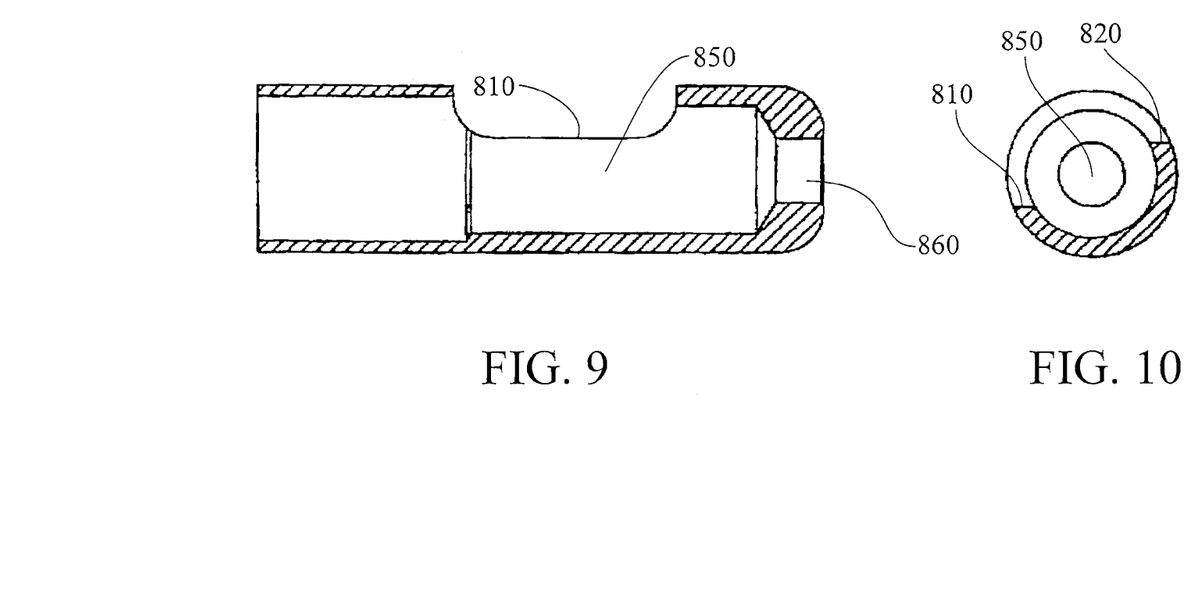
FIG. 9 is a sectional view of FIG. 8 taken along line 9-9.
FIG. 10 is a sectional view of FIG. 9 taken along line 10-10.

FIGS. 8-10 show yet another embodiment of a scraping element 800 in which the edges of the reservoir 850 are asymmetrical relative to each other. In particular, the reservoir 850 comprises edges 810, 830 which are located along different planes, as shown in the cross-sectional view of FIG. 10. Having the edges 810 and 830 reside in different planes creates an unleveled reservoir 850. The unleveled reservoir 850 may possess the ability to remove an increasing amount of tissue cells as the scraping element 800 is rotated clockwise and/or counterclockwise. The scraping element 800 also comprises an aperture 860 through which a wire guide may extend through. The aperture 860 may be sized to receive the wire guide.

The various scraping elements described above may be formed from any suitable metallic alloy, including stainless steel and nitinol. Additionally, the scraper elements may be formed from any suitable biocompatible polymer known to one of ordinary skill in the art.

Figure 11:
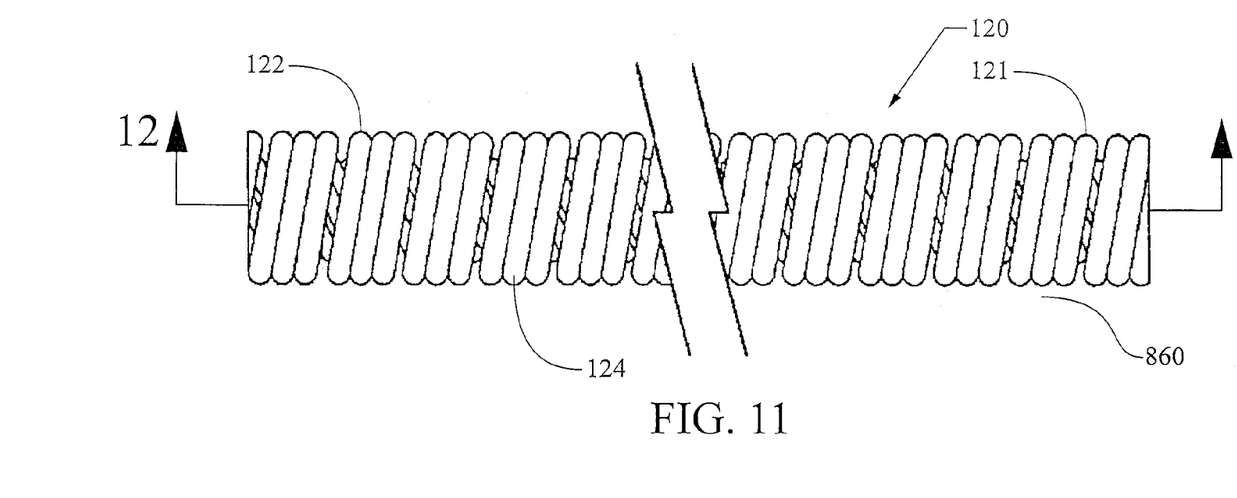
FIG. 11 is an external view of a coiled shaft that affixes to a cytology scraper.
Figure 12:
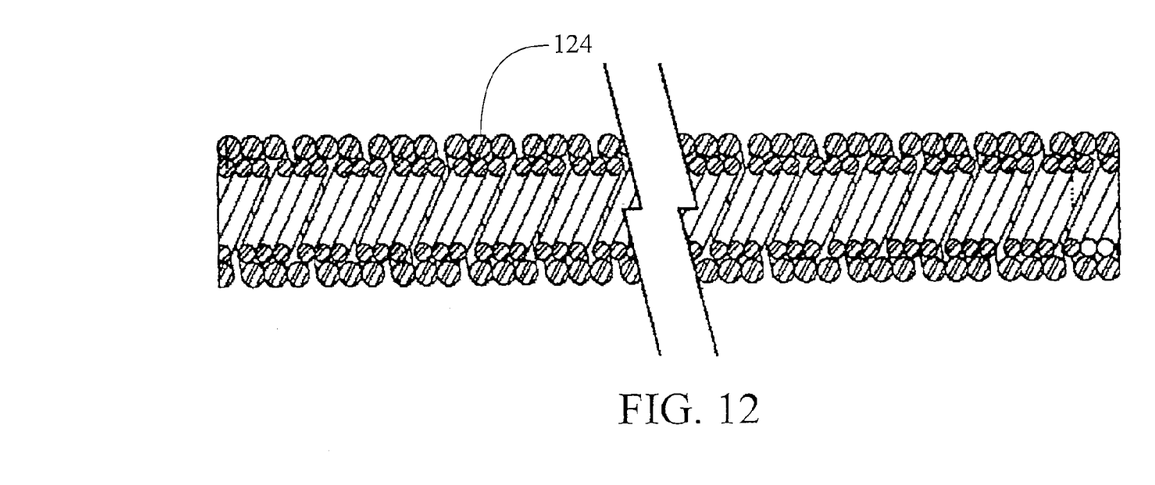
FIG. 12 is a sectional interior view of FIG. 11 taken along line 12-12

A blown-up view of the shaft 120 is shown in FIGS. 11 and 12. FIG. 11 shows an external view of the coiled shaft 120 of FIG. 1. The coiled shaft 120 is hollow and may affix to the above-described cytology scrapers by a threaded connection. Other means for connecting the coiled shaft 120 to the scrapers are contemplated, such as soldering or glue. The scraping element may also be detachable from the coiled shaft 120. In one example, the scraping element may comprise internal threads which removably engage with external threads of coiled shaft 120 along a distal portion of the coiled shaft 120. Having a detachable scraping element enables the scraping element to disengage from the shaft 120 and thereafter be taken for laboratory analysis. A new scraping element 110 can then be affixed to the coiled shaft 120 for a subsequent procedure.

FIG. 12 shows a double layer coil. The inner coil has an opposite pitch to that of the outer coil as shown in FIG. 11. The coiled shaft 120 comprises individual filaments 124

(FIG. 12) which wrap around the longitudinal axis of the shaft 120 in a helical manner. The shaft 120 possesses torsional rigidity which imparts pushability and flexibility to the shaft 120 thereby facilitating advancement through a body lumen. The coiled shaft 120 may be formed from any suitable biocompatible material, including nitnol and stainless steel alloy. Additionally, the individual filaments 124 may be coated with a hydrophilic polymeric material (e.g., polytetrafluoroethylene) to promote wetability of the surface of the shaft 120 as it navigates through the body lumen, thereby reducing the frictional engagement of the filaments 124 with the walls of the body lumen. The reduced frictional engagement reduces trauma incurred by the patient during the cytology procedure. The reduced fiction and flexibility of the shaft 120 enables it to be navigated through the body lumen of the patient, as well as to flex and bend during the cytology procedure, which will be described below. Alternatively and/or additionally, an outer diameter of the coiled shaft 120 may be coated with a heat shrink material that reduces frictional engagement of the filaments 124 with the walls of the body lumen.

Referring to FIG. 11, the coiled shaft 120 includes a distal portion 122 and a proximal portion 121. The distal portion 122 of the shaft 120 is designed to be introduced into a body lumen of a patient, where the sampling procedure is to be performed. The proximal portion 121 of the shaft 120 is designed to remain outside of the patient's body so that the distal portion 122 of the coiled shaft 120 may be manipulated inside a body lumen by a physician handling the control handle 130 (FIG. 1). The coiled shaft 120 preferably has a length ranging between about 120 centimeters and about 240 centimeters, and more preferably, between about 150 and about 210 centimeters. The coiled shaft 120 preferably has an outer diameter ranging between about 5 FR and about 14 FR.

Figure 13:
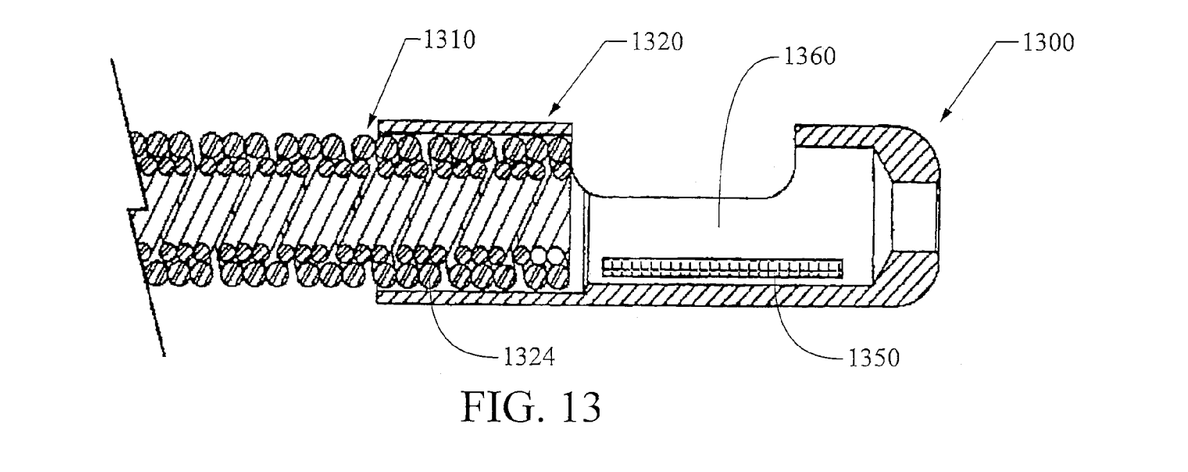
FIG. 13 is a partial side view of the coiled shaft of FIG. 11 affixed within a cytology scraper, the cytology scraper having a mesh disposed within a bottom surface of a reservoir.

FIG. 13 shows a cytology scraper 1300 in which a distal portion of an outer diameter of a coiled shaft 1310 is affixed to a proximal portion of an inner diameter of a scraping element 1320. The coiled shaft 1310 may affix to the scraping element 1320 in numerous ways. In one example, filaments 1324 of the shaft 1310 may soldered to the inner diameter of the scraping element 1320. In another example, the filaments 1324 may be glued to the inner diameter of the scraping element 1320.

Still referring to FIG. 13, a mesh 1350 is shown disposed within a bottom surface of the reservoir 1360. The mesh 1350 retains the removed tissue cells and prevents the tissue cells from falling out of the reservoir 1360 during the cytology procedure. The mesh 1350 may be a removable mesh-like structure which traps the tissue cells within the interstices of the mesh, thereby improving the retention capability of the scarping element 1300. The mesh 1350 may be permanently attached to the tip. The mesh 1350 acts as a mechanical trap to keep tissue within the tip of the cytology device.

Figure 14:
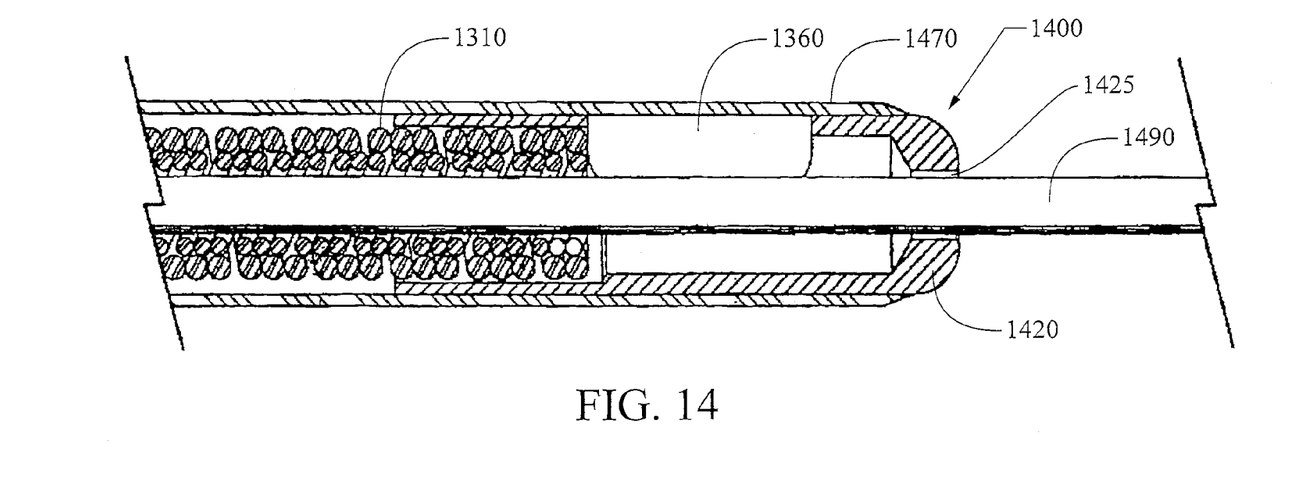
FIG. 14 is a partial side view of the spring shaft of FIG. 11 affixed within a cytology scraper having a wire guide extend therethrough and a retractable outer sheath disposed over the scraping element.

FIG. 14 shows an alternative embodiment of a cytology scraper 1400 in which the mesh 1350 of FIG. 13 is replaced with a retractable outer sheath 1470. FIG. 14 shows the retractable outer sheath 1470 disposed completely over the reservoir 1360 of the scraping element 1420 during deployment to a target tissue site. The sheath 1470 may prevent the edges of the scraping element 1420 from inadvertently injuring healthy tissue. The sheath 1470 may also be disposed completely over the reservoir 1360 of the scraping element 1420 during withdrawal from the target tissue site for the purpose of preventing the captured tissue cells from inadvertently falling out of the reservoir 1360. A wire guide 1490 is also shown extending through the cytology scraper 1400 and distally emerging from aperture 1425 of the scraping element 1420.

The wire guide lumen may have several variations. For example, the wire guide lumen may extend only within a distal portion such that only a distal end of the wire guide 1490 is within the lumen, thereby enabling a short wire guide exchange or release of the wire guide 1490 from the scraper 1400. The details of the method for a short wire guide exchange are disclosed in U.S. Publication No. 2005-0070794 A1, published on Mar. 31, 2005, which is incorporated herein by reference. Alternatively, the wire guide lumen may extend the entire length of the shaft 1310 to support both short and long wire guide exchanges.

Although a single wire guide lumen is shown, additional lumens may also be disposed through the scraping element 1420 and coiled shaft 1310. For example, a second lumen may be employed to inject contrast media. The second lumen may exit through a second aperture adjacent to or spaced away from the first aperture 1425 of the scraping element 1420.

In an alternative embodiment, the cytology scraper may comprise a tapered scraping element The tapered scraping element may be pushed through the stricture, thereby dilating the stricture as it is pushed therethrough. The edges may scrape tissue cells during the dilation of the stricture.

Figures 15, 16:
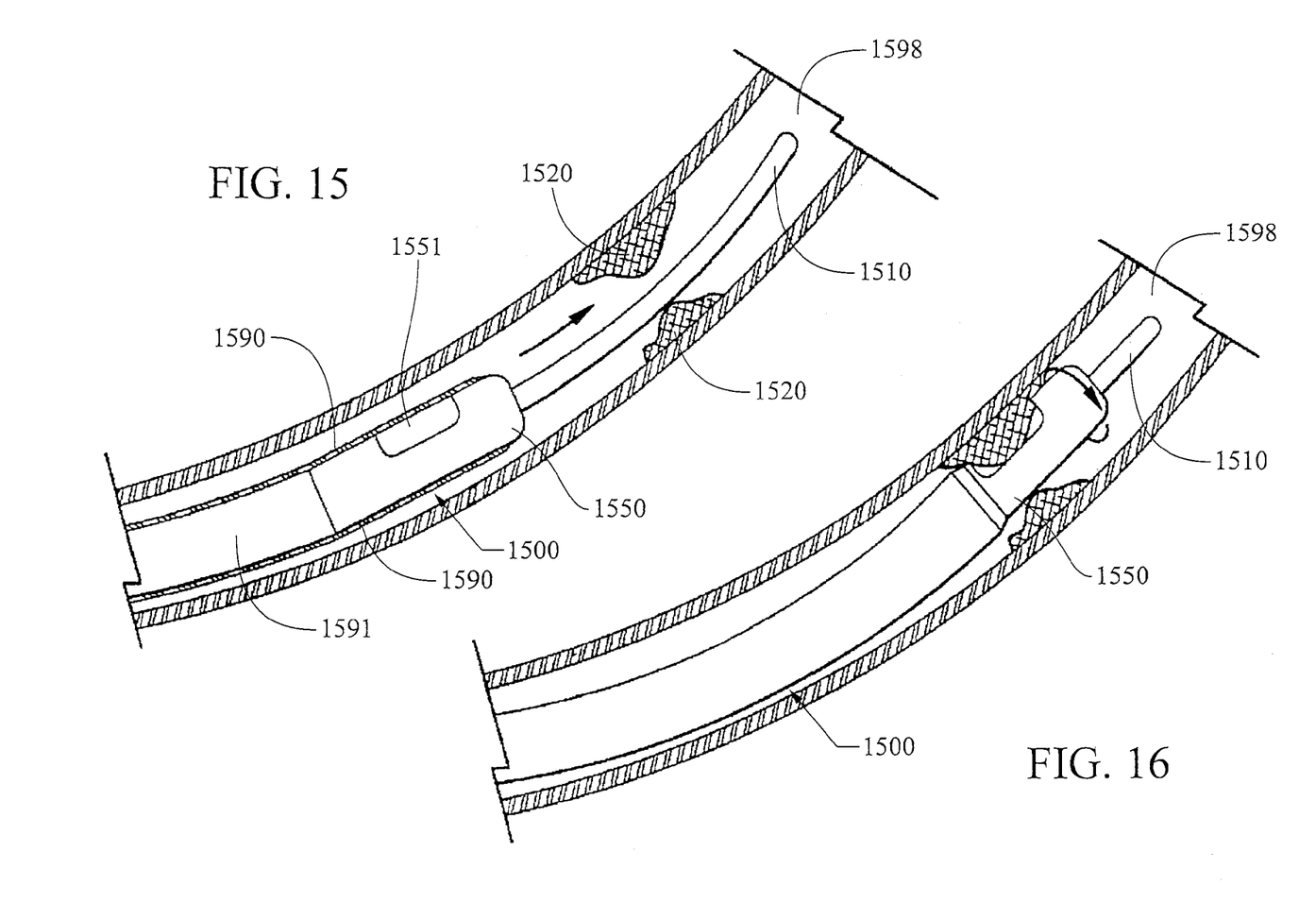
FIG. 15 is a side view of a cytology scraper advancing towards a target tissue site, the cytology scraper advancing over a wire guide and an outer sheath disposed over a scraper element of the cytology scraper.
FIG. 16 is a side view of the cytology scraper of FIG. 15 showing the outer sheath retracted such that the scraper element is exposed and thereafter rotated about its longitudinal axis to remove tissue cells from the target tissue site.

Having described the structural elements of the cytology scraper, an example of a method of its use within the gastrointestinal tract will now be described with respect to FIGS. 15 and 16. The method of use will be described using the cytology scraper 100 described in the embodiment of FIGS. 1-4. A physician may advance an endoscope (not shown) within a desired region of the gastrointestinal lumen where the target tissue to be removed is located. The distal end of the endoscope is advanced in close proximity to the target tissue 1520. With the endoscope deployed in a desired position, a wire guide 1510 (FIG. 15) may be loaded through the accessory channel of the endoscope until it emerges from the distal end of the channel and extends towards the target tissue 1520. After the surgeon has positioned the wire guide 1510 in close proximity to the target tissue 1520, the cytology scraper 100 may be loaded into the accessory channel. In particular, the wire guide lumen of the coiled shaft 120 and the cytology scraper 100 receives the wire guide 1510, which serves as a stable guide to facilitate deployment of the cytology scraper 100. The physician may maneuver a control handle 130, as shown in FIG. 1, to aid in manipulating the scraper element 110 towards the target tissue 1520. During the advancement of the scraper element 110 towards the target tissue 1520, an outer sheath 1590 may be disposed completely over the reservoir 140 of the scraping element 110, which may prevent inadvertent puncture and/or trauma of the normal tissue within the body lumen 1598. The outer sheath 1590 may also prevent the inadvertent collection of tissue from elsewhere along the body lumen (i.e., non-target tissue). Alternatively or in addition, a mesh 1350 may be affixed to or disposed within the reservoir 140.

After the scraper element 110 has reached the target tissue 1520 (FIG. 16), the cytology sampling procedure may begin. The outer sheath 1590 is retracted back to at least expose the reservoir 140 of the scraping element 110. The physician may apply a suitable amount of torque at the control handle 130 (FIG. 1) to cause the scraper element 110 to rotate in a clockwise and/or counterclockwise direction as indicated by the arrows in FIG. 16. The rotation of the scraper element 110 enables the edges 141-144 (FIG. 1) of the reservoir 140 to scrape away cells from the target tissue 1520. Alternatively, or in addition, the scraper element 110 may also engage the target tissue 1520 via back and forth movements to scrape away cells. Reservoir 140 may help to trap the tissue after it is scraped off from the body lumen. A mesh 1350 may be disposed within the reservoir 140 to trap the removed tissue cells, thereby increasing retention of the removed tissue cells and preventing the tissue cells from falling out of the reservoir 140.

During the cytology procedure, the strictures at target tissue site 1520 may be dilated as the exposed edges 141-144 (FIG. 1) and surfaces of the scraping element 110 rub therealong. The scraper element 110 is relatively stiff thereby providing adequate radial force to dilate a stricture. Additionally, the coil spring structure may provide sufficient pushability to pass through the stricture. The scraping and dilating functions by the scraper element 110 can be achieved simultaneously. This is advantageous over current procedures, which require subsequent introduction of a dilation catheter for purposes of implanting a stent at the target site after a cytology brush has obtained the required tissue sample and has been withdrawn from the target site.

After a sufficient amount of cells have been scraped and deposited into reservoir 140, the outer sheath 1590 may resheath the reservoir 140 to retain the captured tissue cells within the reservoir 140. Having resheathed the reservoir 140, the cytology scraper 100 is withdrawn from the body lumen 1598. Upon withdrawal, the scraped cells are removed from the reservoir 140 in order for subsequent sampling of the cells to be conducted.

The cytology scraper of the above described embodiments may be used without an endoscope and in other areas besides the gastrointestinal lumen. As can be seen, unlike conventional cytology brushes, the above-described cytology scrapers are capable of removing a greater amount of tissue cells and retaining the cells within the device until sampling can begin. The cytology scraper of the above described embodiments offers a more aggressive approach to obtaining tissue samples compared to conventional brushes and other biopsy devices.

The specific design features of the cytology scraper described in the above embodiments possess numerous advantages over conventional biopsy devices. For example, the cytology scraper structural design enables it to extract an increased amount of issue compared to conventional biopsy devices. Additionally, the cytology scraper can be rotated at a target site to yield tissue cells which isolates the location from which the sample is being taken. Conventional biopsy devices must be advanced and retracted along the target tissue site, which increases the chance that tissue cells may be erroneously obtained proximally and/or distally of the target tissue site. Still further, conventional biopsy devices such as forceps can only bite in the forward direction. Thus, utilizing forceps to obtain biopsy samples about the circumference of a duct is difficult. The cytology scraper can readily be rotated to obtain biopsy samples about the circumference of a duct.

The above figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. A cytology device, comprising:
a helically coiled cable comprising torsional rigidity sufficient to transfer rotational motion from a proximal portion of the cable to a distal portion of the cable, the distal portion adapted to be introduced into a body lumen, the proximal portion adapted to remain outside of the lumen so as to allow manipulation of the distal portion;
a cylindrical-shaped scraper element operably connected to the distal portion, the scraper element comprising an opening disposed in an exterior surface thereof, the opening being proximal of and spaced apart from a distal end of the scraper element, the opening bounded by a pair of longitudinally oriented edges and a pair of circumferentially oriented edges, at least one of the pair of longitudinally oriented edges comprising a cutting edge configured to excise tissue cells upon rotational movement of the scraper element; and
a reservoir adapted to receive the excised tissue, the reservoir being disposed within the scraper element and adjacent to the at least one cutting edge, the reservoir having a longitudinal length that is greater than a longitudinal length of the opening and extends distally of the opening.

2. The cytology device of claim 1, further comprising a mesh configured to retain the cells, the mesh being disposed within the reservoir and spaced apart from the at least one cutting edge.

3. The cytology device of claim 1, further comprising a retractable outer sheath movably disposed over the reservoir, the sheath being configured to close the opening of the scraper element by engaging each of the pair of longitudinally oriented edges and each of the pair of circumferentially oriented edges.

4. The cytology device of claim 1, wherein the pair of longitudinally oriented edges comprises a first cutting edge and a second cutting edge, the first and the second cutting edges being disposed along opposite sides of the opening of the scraping element.

5. The cytology device of claim 4, wherein the first and the second cutting edges comprise cutting surfaces that are disposed along the same plane.

6. The cytology device of claim 4, wherein the first and the second cutting edges are disposed along different planes to create an asymmetrical scraper element.

7. The device of claim 1, wherein a wire guide extends through a wire guide lumen and exits through a distal aperture disposed in the distal end of the scraper element, the distal aperture being spaced apart from the opening.

8. The cytology device of claim 1, wherein the at least one cutting edge is recessed within the exterior surface of the scraper element.

9. The cytology device of claim 1, wherein the at least one cutting edge is disposed along the exterior surface of the scraper element.

10. The cytology device of claim 1, wherein at least one of the pair of circumferentially oriented edges comprises a second cutting edge that generally extends along a plane that is perpendicular to the longitudinal axis of the device, the second cutting edge being configured to excise tissue cells upon longitudinal movement of the scraper element.

11. The cytology device of claim 1, wherein the scraper element comprises four cutting edges, each of the edges being disposed along a perimeter of the opening and adjacent to the reservoir.

12. The cytology device of claim 1, the scraper element comprising an outer circumference, the at least one cutting edge being disposed along the outer circumference.

13. A cytology device, comprising:
a helically coiled cable comprising torsional rigidity sufficient to transfer rotational motion from a proximal portion of the cable to a distal portion of the cable;

a scraper element operably connected to the distal portion, the scraper element comprising an opening bounded by a plurality edges, the plurality of edges comprising a first cutting edge configured to excise tissue cells upon rotational movement of the scraper element and a second cutting edge configured to excise tissue cells upon longitudinal movement of the scraper element, a reservoir adapted to receive the excised tissue, the reservoir being disposed within the scraper element and adjacent to the opening; and a retractable outer sheath movably disposed over the scraper, element for retaining excised tissue within the reservoir, the outer sheath configured to engage each of the plurality of edges to close the opening of the scraper element.

14. The device of claim 13, wherein the opening of the scraper element is bounded by four edges, wherein each of the four edges comprises a cutting edge.

15. The device of claim 13, wherein a distal end of the scraping element comprises a second opening adapted for a wire guide to extend therethrough.

16. The device of claim 13, wherein an inner diameter of a proximal end of the scraping element is removably engaged to an outer diameter of a distal end of the coiled cable.

17. A method of performing a cytology procedure, comprising the steps of:
(a) providing a cytology device comprising:
a helically coiled cable comprising torsional rigidity sufficient to transfer rotational motion from a proximal portion of the cable to a distal portion of the cable, the distal portion adapted to be introduced into a body lumen, the proximal portion adapted to remain outside of the lumen so as to allow manipulation of the distal portion; and a cylindrical-shaped scraper element operably connected to the distal portion, the scraper element comprising an opening disposed in an exterior surface thereof, the opening being proximal of and spaced apart from a distal end of the scraper element, the opening bounded by a pair of longitudinally oriented edges and a pair of circumferentially oriented edges, at least one of the pair of longitudinally oriented edges comprising a cutting edge configured to excise tissue cells upon rotational movement of the scraper element; and a reservoir adjacent to the at least one cutting edge and adapted to receive the excise tissue, the reservoir being disposed within the scraper element and adjacent to the at least one cutting edge, the reservoir having a longitudinal length that is greater than a longitudinal length of the opening and extends distally of the opening;

(b) advancing the cytology device to the target tissue site;
(c) rotating the proximal portion of the coiled cable so as to engage and excise the target tissue with the cutting edges; and
(d) collecting tissue cells in the reservoir.

18. The method of claim 17, wherein the engaging step comprises at least one of moving the scraping element with back and forth movements against the target tissue site and rotating the scraping element against the target tissue site.

19. The method of claim 17, further comprising the step of:
(e) dilating a stricture within a body lumen.

20. The method of claim 19, further comprising the step of:
(f) withdrawing the cytology device from the target tissue site; and
(g) detaching the scraping element from the coiled cable.

* * * * *